(12) United States Patent
Kobayashi et al.

(10) Patent No.: US 9,951,305 B2
(45) Date of Patent: Apr. 24, 2018

(54) CELL CULTURE DEVICE AND TRANSPORT DEVICE

(75) Inventors: Toyoshige Kobayashi, Tokyo (JP);
Ryota Nakajima, Tokyo (JP);
Takayuki Nozaki, Tokyo (JP); Shizu Matsuoka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 273 days.

(21) Appl. No.: 14/111,060

(22) PCT Filed: Apr. 4, 2012

(86) PCT No.: PCT/JP2012/059224
§ 371 (c)(1),
(2), (4) Date: Nov. 26, 2013

(87) PCT Pub. No.: WO2012/141055
PCT Pub. Date: Oct. 18, 2012

(65) Prior Publication Data
US 2014/0087455 A1     Mar. 27, 2014

(30) Foreign Application Priority Data

Apr. 13, 2011 (JP) ................................ 2011-089324
Apr. 13, 2011 (JP) ................................ 2011-089325

(51) Int. Cl.
*C12M 1/00* (2006.01)
*C12M 1/12* (2006.01)

(52) U.S. Cl.
CPC ............ *C12M 29/00* (2013.01); *C12M 23/14* (2013.01); *C12M 23/50* (2013.01); *C12M 37/00* (2013.01); *C12M 41/14* (2013.01)

(58) Field of Classification Search
CPC ....... C12M 23/44; C12M 23/46; C12M 23/48
See application file for complete search history.

(56) References Cited

U.S. PATENT DOCUMENTS

| 6,943,008 B1 * | 9/2005 | Ma ......................... C12M 23/34 435/297.1 |
| 2004/0077072 A1 * | 4/2004 | Takagi ................... C12M 21/08 435/284.1 |

(Continued)

FOREIGN PATENT DOCUMENTS

| JP | 2002-315566 A | 10/2002 |
| JP | 2006-149268 A | 6/2006 |

(Continued)

OTHER PUBLICATIONS

Extended European Search Report dated Nov. 7, 2014 (five (5) pages).

(Continued)

*Primary Examiner* — Sean E Conley
*Assistant Examiner* — Matthew D Krcha
(74) *Attorney, Agent, or Firm* — Crowell & Moring LLP

(57) ABSTRACT

The present invention provides a carrier device including a culture vessel and a flow channel, which have a closed structure, for supplying cell liquid or a culture medium into the flow channel; and a method of aseptically injecting liquid, such as the cell or the culture medium, into the culture vessel and the flow channel. The present invention provides a carrier jig 19 including a drive base 27, a culture vessel base 21 that holds a culture vessel 20, a culture medium base 32 that holds a cell bag 60 and the like for the culture medium and the cell, and a detachable flow channel 40, those of which are held by a lift 98 to be carried to a cell culture device. A part of the flow channel 40 and the cell bag 60 mounted on the carrier jig 19 are put into a clean space 78. The cell and the culture medium are supplied into the flow channel 40 by using the cell bag 60 and other bags in the clean space, and then, an injection port 89 is closed. The respective bases and the flow channel are simultaneously (Continued)

mounted to the cell culture device by using the carrier jig 19. Thus, the aseptic cell culture can be realized.

21 Claims, 15 Drawing Sheets

(56) References Cited

U.S. PATENT DOCUMENTS

| | | | | |
|---|---|---|---|---|
| 2004/0126876 | A1* | 7/2004 | Ravin | B01L 3/508 435/288.3 |
| 2004/0147012 | A1* | 7/2004 | Yokoi | C12M 23/48 435/303.1 |
| 2006/0115889 | A1 | 6/2006 | Nakashima et al. | |
| 2006/0257999 | A1* | 11/2006 | Chang | B01J 19/0046 435/289.1 |
| 2006/0289371 | A1* | 12/2006 | Malin | A61B 10/0096 211/40 |
| 2009/0029445 | A1* | 1/2009 | Eckelberry | C12M 21/02 435/257.1 |
| 2009/0269841 | A1* | 10/2009 | Wojciechowski | C12M 23/28 435/325 |
| 2012/0164721 | A1 | 6/2012 | Kobayashi et al. | |
| 2013/0143307 | A1 | 6/2013 | Nozaki et al. | |

FOREIGN PATENT DOCUMENTS

| | | |
|---|---|---|
| JP | 2007-312668 A | 12/2007 |
| JP | 2008-113600 A | 5/2008 |
| JP | 2011-142837 A | 7/2011 |
| JP | 2012-130297 A | 7/2012 |
| JP | 2012-217436 A | 11/2012 |
| JP | 2013-31461 A | 2/2013 |
| JP | 2012-217435 A | 11/2013 |
| WO | WO 2011/087053 A1 | 7/2011 |
| WO | WO 2012/020458 A1 | 2/2012 |

OTHER PUBLICATIONS

Korean Office Action dated Mar. 30, 2015 (five (5) pages).
International Search Report dated May 1, 2012 with English translation (five (5) pages).

* cited by examiner

CELL CULTURE DEVICE AND TRANSPORT DEVICE

TECHNICAL FIELD

The present invention relates to a cell culture device that cultures a cell, and more particularly to an automatic culture technique efficiently culturing a cell with aseptic cleanness.

BACKGROUND ART

Conventionally, a cell culturing work has manually been done by a skilled worker in a clean room, which is disinfected as much as possible, under a strict manufacturing process. Therefore, when a lot of cells are cultured for industrialization, a burden on a worker might increase, time and cost required for education and development of the worker might increase, a human error might occur, a specimen might wrongly be taken, or a biological contamination by human having bacteria might occur. Much cost has to be taken for solving these problems. This becomes a big hurdle for the industrialization of culturing a lot of cells.

Therefore, it has been expected that these problems are solved by automating a series of the culturing work by a device. In view of this, an automated cell culture device that imitates a manual culturing work has been mainly developed in recent days by using an articulated robot manipulator. However, since the manual culturing work is made by complicated actions, the automated culture device needs to aseptically handle a culture vessel and culture solution in a level equal to the manual handling, or in a simplified level.

In order to realize this, Patent Literature 1 provides an example of carrying a culture vessel or performing a medium replacement by using an articulated robot manipulator, for example. The robot manipulator described in Patent Literature 1 has a self-sterilizing structure.

Patent Literature 2 proposes a method in which a culture vessel and a flow channel are in a closed system, for example. This method is for a device that has a culture vessel and a flow channel provided in a closed system for culturing chondrocyte cell under a high pressure, and this method is for extracting the culture cell and the flow channel, a part of which is plugged, without being exposed to the open air after the culture process is finished. This method includes a unit for collecting the chondrocyte cell that is aseptically generated.

CITATION LIST

Patent Literature

PTL 1: Japanese Patent Application Laid-Open No. 2006-149268
PTL 2: Japanese Patent Application Laid-Open No. 2002-315566

SUMMARY OF INVENTION

Technical Problem

In the automated culture device described in Patent Literature 1, the culture vessel is an open system, so that an action of opening a lid to open the culture vessel is required. Therefore, the device entails an increased size of an air-conditioning device for keeping cleanness in the automated culture device. Accordingly, the entire system becomes large-sized, so that cost is also increased.

The automated culture device described in Patent Literature 2 uses the closed system, so that the problem is how to mount the flow channel and how to inject a culture medium (culture solution) or a cell (cell suspension) into the flow channel with the inside aseptic property being maintained. Another problem is how to easily install the closed flow channel to the device and how to efficiently apply driving force, upon executing the complicated culturing operation.

In a regenerative medicine for transplanting a cell or tissue created by a culture by using a human cell, a tissue collected in an operation room is put into an aseptic test tube and carried out in the aseptic condition, a required cell is isolated from the tissue in a clean room (CPC: Cell Processing Center) according to Good Manufacturing Practice (GMP), and the cell is cultured by performing an intended adjustment. In order to culture the collected cell with no contamination at all during a manufacturing process, the cell has to be manufactured manually under a process and environment complying with a more strict regulation. Even in the automated culture device that mechanically and automatically cultures the cell, the cell or tissue produced by this device must not biologically be contaminated by bacteria or virus during the manufacturing process. Considering the system in the automated culture device using the open-type culture vessel described above under such condition, a huge air-conditioning facility and a sterilizing facility are needed to sterilize the inside of the automated culture device and keep the inside in a high clean environment, whereby the production cost and the maintenance cost for these facilities are needed. A drive system such as a motor does not withstand the sterilizing process.

Therefore, a preferable system for culturing a cell is such that the culture vessel for the automatic culture has a closed structure, the inside of the vessel can be sterilized, and driving force is externally applied. However, in order to culture a cell in the culture vessel having the closed structure, a flow channel has to be formed. The problem is how to minimize the production error of the closed flow channel, and how to provide the closed structure efficiently, safely, and aseptically. Further, in order to culture a cell in the culture vessel having the closed structure, another problem is how to simplify and realize an efficient mechanism and control for performing the culture process by putting a culture medium or a cell aseptically.

In order to solve the problems described above, an object of the present invention is to provide a cell culture device having a mechanism for aseptically mounting a closed flow channel to a driving system.

In order to solve the problems described above, another object of the present invention is to provide a carrier device for aseptically supplying cell liquid into the closed flow channel of the cell culture device, and a method of aseptically injecting liquid such as the cell liquid.

Solution to Problem

In order to attain the foregoing objects, the present invention provides a cell culture device for culturing a cell by using a culture medium, the device including: a first module including multiple bags having the culture medium and the cell, and a first flow channel group that supplies the culture medium and the cell from some of the multiple bags and exhausts the culture medium and the cell to some other bags of the multiple bags; a second module including a culture vessel for culturing the cell, and a second flow channel group that supplies the culture medium and the cell to the culture vessel and exhausts the culture medium and the cell from the culture vessel; a tank unit including an injection tank that holds the culture medium and the cell supplied from a flow channel in the first flow channel group, and allows the held culture medium and the cell to flow out to a flow channel in the second flow channel group in order to supply the culture medium and the cell to the culture vessel, and a waste tank that holds the culture medium and the cell, which are exhausted from the culture vessel and flown from the flow channel in the second flow channel group, and allows the held culture medium and the cell to flow out to the flow channel in the first flow channel group in order to exhaust the culture medium and the cell to some other bags of the multiple bags; and a third module including a pump unit that controls a volume of the supplied culture medium and the cell in the flow channels in the first and second flow channel groups and a volume of the culture medium and the cell held in the tank unit.

In order to attain the foregoing objects, the present invention provides a cell culture device for culturing a cell by using a culture medium, the device including: a first module including multiple bags having the culture medium and the cell, and a first flow channel group that supplies the culture medium and the cell from some of the multiple bags and exhausts the culture medium and the cell to some other bags of the multiple bags, the first module being held by a holding base; a second module including a culture vessel for culturing the cell, and a second flow channel group that supplies the culture medium and the cell to the culture vessel and exhausts the culture medium and the cell from the culture vessel, the second module being held by the holding base; a tank unit including an injection tank that holds the culture medium and the cell supplied from a flow channel in the first flow channel group, and allows the held culture medium and the cell to flow out to a flow channel in the second flow channel group in order to supply the culture medium and the cell to the culture vessel, and a waste tank that holds the culture medium and the cell, which are exhausted from the culture vessel and flown from the flow channel in the second flow channel group, and allows the held culture medium and the cell to flow out to the flow channel in the first flow channel group in order to exhaust the culture medium and the cell to some other bags of the multiple bags; and a third module including a pump unit that controls a volume of the supplied culture medium and the cell in the flow channels in the first and second flow channel groups and a volume of the culture medium and the cell held in the tank unit, the third module being held by the holding base.

Specifically, in order to attain the foregoing objects, according to the preferable embodiment of the present invention, the closed flow channel includes three module groups. The module groups include a culture medium module containing cell liquid, culture medium, cleaning liquid, or waste liquid, which needs to be refrigerated, a pump module that feeds these liquids into a culture chamber by using a pump, and warms these liquids in a tank, and a culture vessel module that supplies the cell liquid or the culture medium into a culture space in the culture vessel from the tank for performing a culture process. A microscope is provided around the culture vessel module, and the cell on the culture face can be imaged. The respective modules are mounted on corresponding holding tools, which are referred to as a holding base, and some of which has a drive mechanism. The closed flow channel can be inserted into and removed from the culture device by a carrier jig that can attach and detach the holding bases. All modules are connected to the tank, so that the modules are not directly connected to one another.

In order to attain the foregoing objects, the present invention also provides a carrier device that can carry multiple bags for a culture medium and a cell to a cell culture device, and that is detachable to the cell culture device, the carrier device including: a first holding tool that holds a culture medium base including multiple bags having the culture medium and the cell, and a first flow channel group that supplies the culture medium and the cell from some of the multiple bags and exhausts the culture medium and the cell to some other bags of the multiple bags; a second holding tool that holds a culture vessel base including a culture vessel for culturing the cell, and a second flow channel group that supplies the culture medium and the cell to the culture vessel and exhausts the culture medium and the cell from the culture vessel; and a third holding tool that holds a drive base including a pump unit that controls a volume of the supplied culture medium and the cell in the flow channels in the first and second flow channel groups.

In order to attain the foregoing objects, the present invention also provides a liquid injecting method for injecting cell liquid into a cell bag that is carried to a cell culture device, the method comprising: carrying a carrier device to a vicinity of a directly cell processing region, the carrier device including a holding tool for holding a culture medium base having multiple bags including the cell bag, and a first flow channel group that supplies the culture medium and the cell from some of the multiple bags and exhausts the culture medium and the cell to the others of the multiple bags, a culture vessel base including a culture vessel that cultures the cell, and a second flow channel group that supplies the culture medium and the cell to the culture vessel, and exhausts the culture medium and the cell from the culture vessel, and a drive base provided with a pump unit that controls the supplied volume of the culture medium and the cell in the flow channel of the first and second flow channel group; moving the cell bag connected to the flow channel to the directly cell processing region from the culture medium base, and injecting the cell into the cell bag in the directly cell processing region; and mounting the cell bag after the injection of the cell on the culture medium base, and then, carrying the same to the cell culture device.

Advantageous Effects of Invention

The present invention can provide a cell culture device that has a property of easily mounting a closed flow channel having a culture vessel, prevents the wrong one from being erroneously set during the manufacture or setting of the flow channel, and efficiently and aseptically cultures a cell with an aseptic cleanness according to a good manufacturing practice.

The present invention can also provide a carrier device having a culture vessel and a flow channel, which have a closed structure, and aseptically supplying cell liquid or a culture medium into the flow channel. The present invention can also provide a liquid injecting method for aseptically injecting cell liquid or a culture medium into a culture vessel and a flow channel.

DESCRIPTION OF EMBODIMENTS

Figure 1:
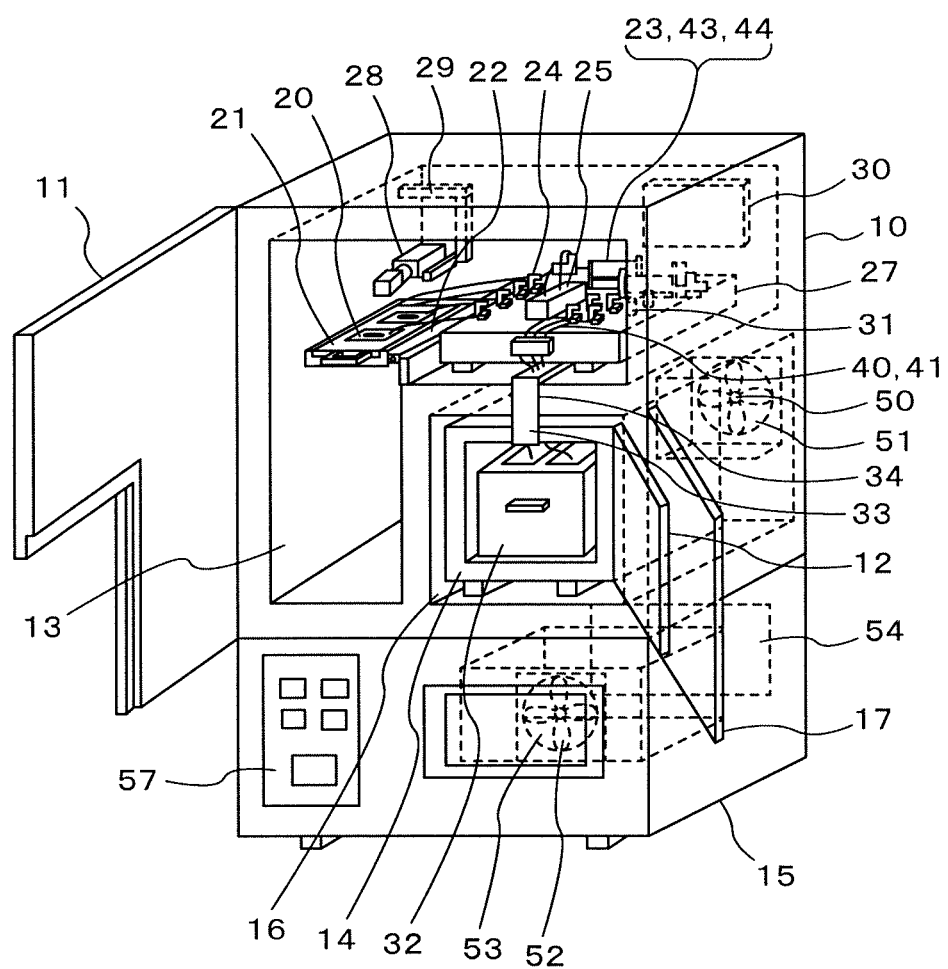
FIG. 1 is a view schematically illustrating an entire configuration of an automated culture device provided with a drive base according to a first embodiment.

One embodiment of the present invention will be described in detail with reference to the accompanying drawings. Before the embodiments will be described in detail, the present invention will be summarized below.

Specifically, in the most preferable embodiment of the automated culture device, cell liquid or a culture medium in a refrigerator (about 4° C.) in the device is warmed in a culture chamber (about 37° C.), and is supplied to a cell culture space in the culture vessel by using a closed flow channel and a mechanism called a drive base for feeding liquid in the closed flow channel. For this process, the closed flow channel mainly includes three modules. These modules are a culture medium module containing cell liquid, culture medium, cleaning liquid, or waste liquid, which needs to be refrigerated, a pump module that feeds these liquids into the culture chamber by using a pump, and warms these liquids up to 37° C. in a tank, and a culture vessel module that feeds the cell liquid or the culture medium into the culture space in the culture vessel from the tank to perform a culture process. A microscope is provided around the culture vessel module, and the cell on the culture face can be imaged. The respective modules are mounted on corresponding holding tools, which are referred to as a holding base, and some of which has a drive mechanism. The closed flow channel can be inserted into and removed from the culture device by a carrier jig that can attach and detach the holding bases. The automated culture device is composed of the culture chamber, a refrigerating chamber, and an intermediate chamber, and each chamber has a door. The inside of refrigerating chamber is kept to be about 4° C., and the inside of the culture chamber keeps an environment close to the environment having a temperature of 37° C., a humidity of 100%, and carbon dioxide of 5%. The cell suspension, the culture medium, the cleaning liquid, and the waste liquid are put into the refrigerating chamber. A waste liquid collecting port with a check valve is provided. The intermediate chamber is provided between the culture chamber and the refrigerating chamber, which have totally a different environment, in order to prevent the occurrence of dew condensation and temperature irregularity caused by the direct connection between the culture chamber and the refrigerating chamber. The culture chamber and the refrigerating chamber are separated by a seal such as a rubber stopper other than a liquid feeding tube. The intermediate chamber is provided with a fan with filter, whereby the environment outside the automated culture device can be kept. According to this configuration, the environment optimum for the cell can be realized, even if totally different environments are present in the same device, and space saving can be realized.

The base is moved near a safety cabinet (or a clean bench) by the carrier jig, an empty bag, which is sterilized, in the closed flow channel is disinfected and put into the safety cabinet, cell suspension (or culture medium or cleaning liquid) is injected into the bag, and an injection port is sealed. According to this process, the inside of the closed flow channel can keep sterilized, regardless of the environment outside the closed flow channel. In the present invention, the closed flow channel is inserted into the automated culture device with the base. Since the drive mechanism is mounted outside the closed flow channel, the automatic cell culture operation, including cell seeding, medium replacement, observation with a microscope, and examination, can be executed with the closed flow channel being kept sterilized, regardless of the place where the automated culture device is mounted.

These and other features of the present invention will be more apparent from the following detailed examples when taken in conjunction with the accompanying drawings. It should be noted that these examples have been presented by way of example only, and are not intended to limit the technical scope of the invention. The same reference numerals are given to the same components in the drawings. In the present specification, terms of a culture vessel base and a culture medium base are used in addition to the above-mentioned drive base. These bases are sometimes collectively referred to as a holding base, since they have a function as a holding tool as described above. First, second, and third holding tools in the carrier device for holding the culture medium base, the culture vessel base, and the drive base are sometimes collectively referred to as a holding tool.

Example 1

An example of a cell culture device that prevents the wrong one from being erroneously set, and includes a mechanism for aseptically and efficiently mounting a closed flow channel to a drive system will be described as an example 1.

Figure 2:
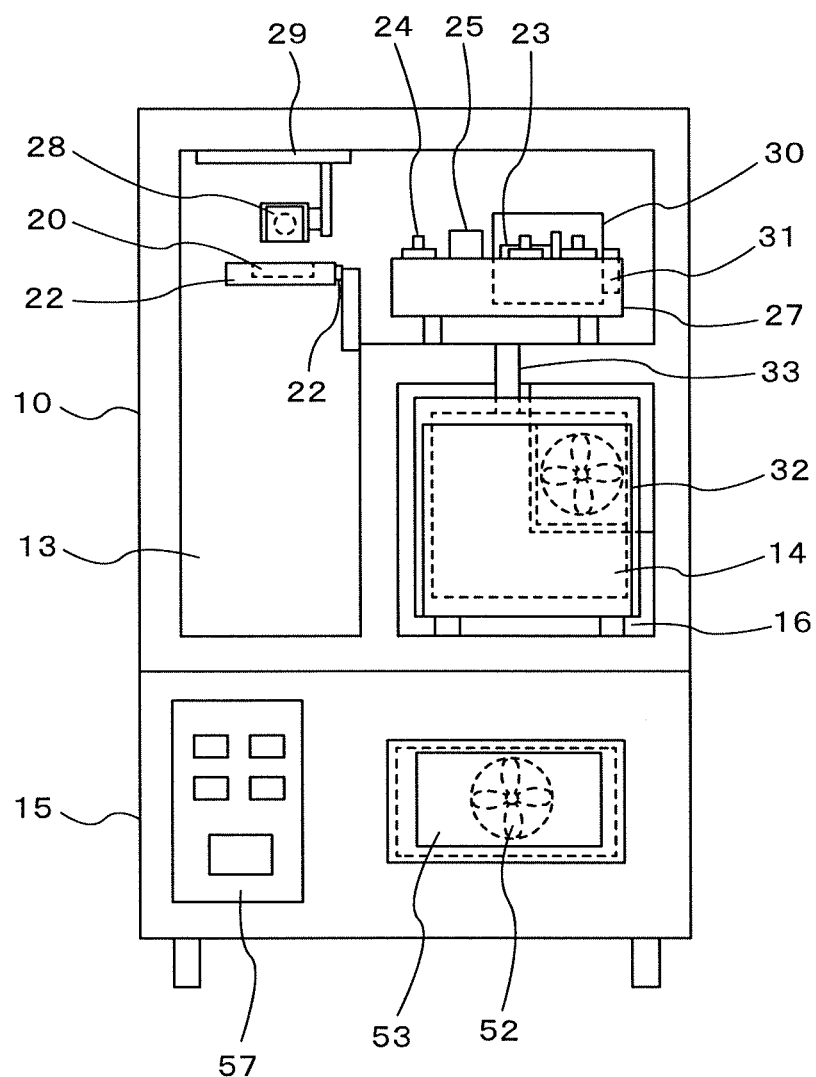
FIG. 2 is a front view illustrating the automated culture device having a door open according to the first embodiment.
Figure 3:
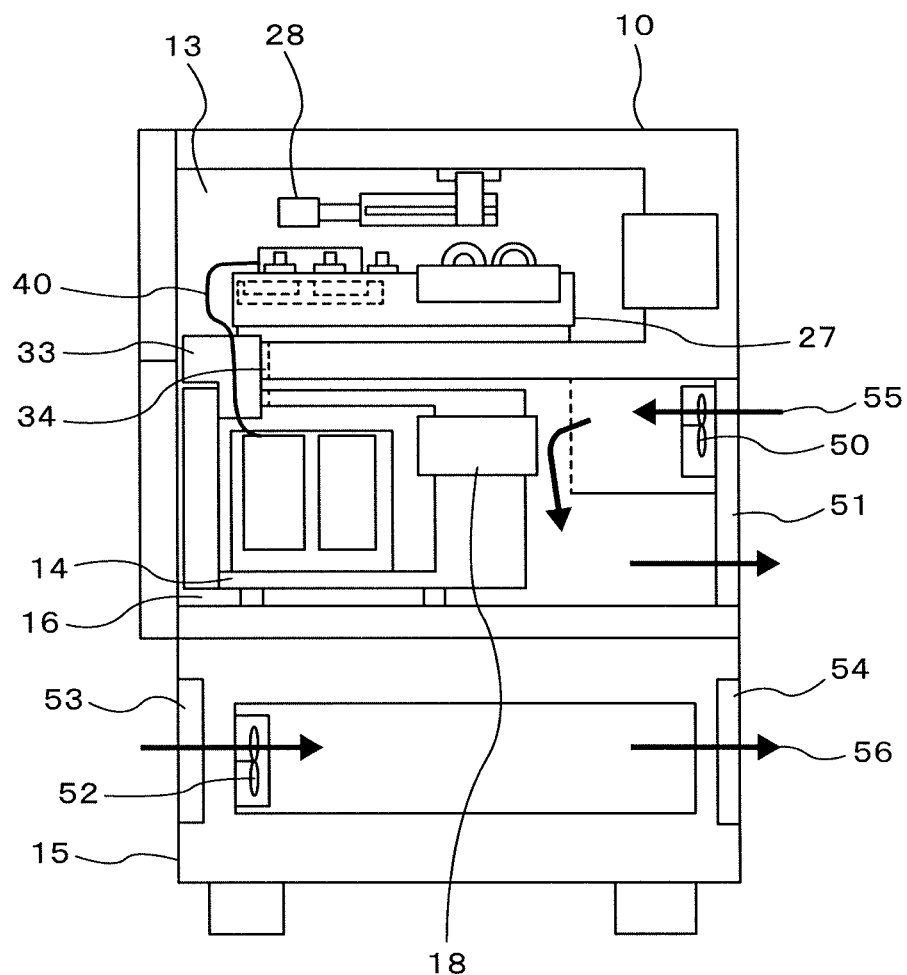
FIG. 3 is a side view illustrating the inside of the automated culture device according to the first embodiment.
Figure 4A:
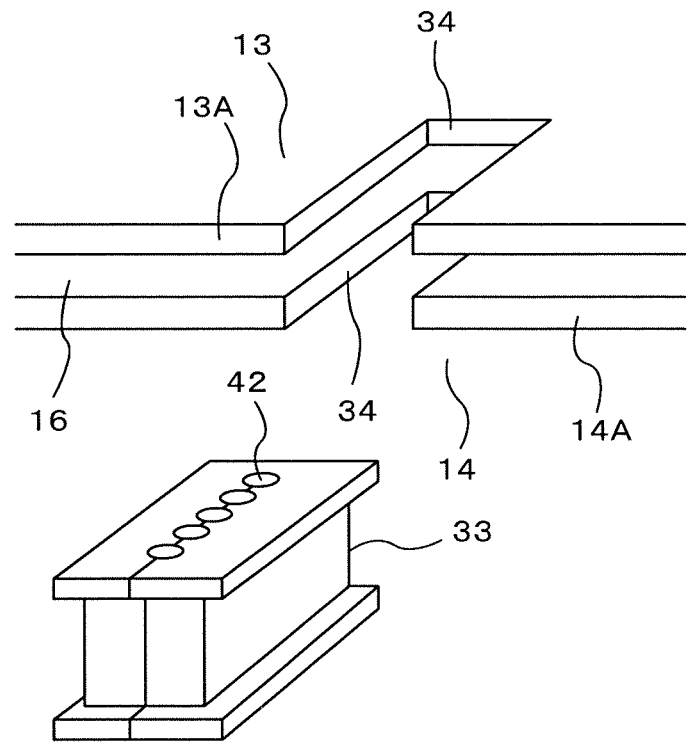
FIG. 4A is a structural view illustrating a state before a seal mechanism is connected to a claw according to the first embodiment.
Figure 4B:
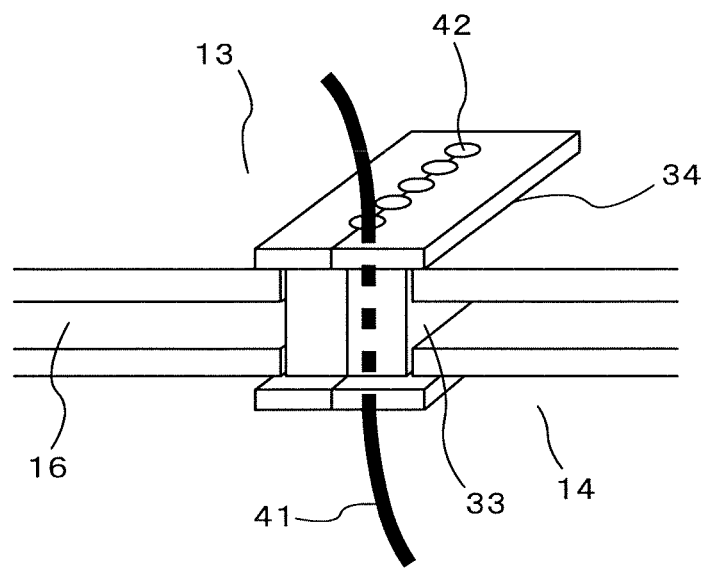
FIG. 4B is a structural view illustrating a state after the seal mechanism is connected to the claw according to the first embodiment.
Figure 5:
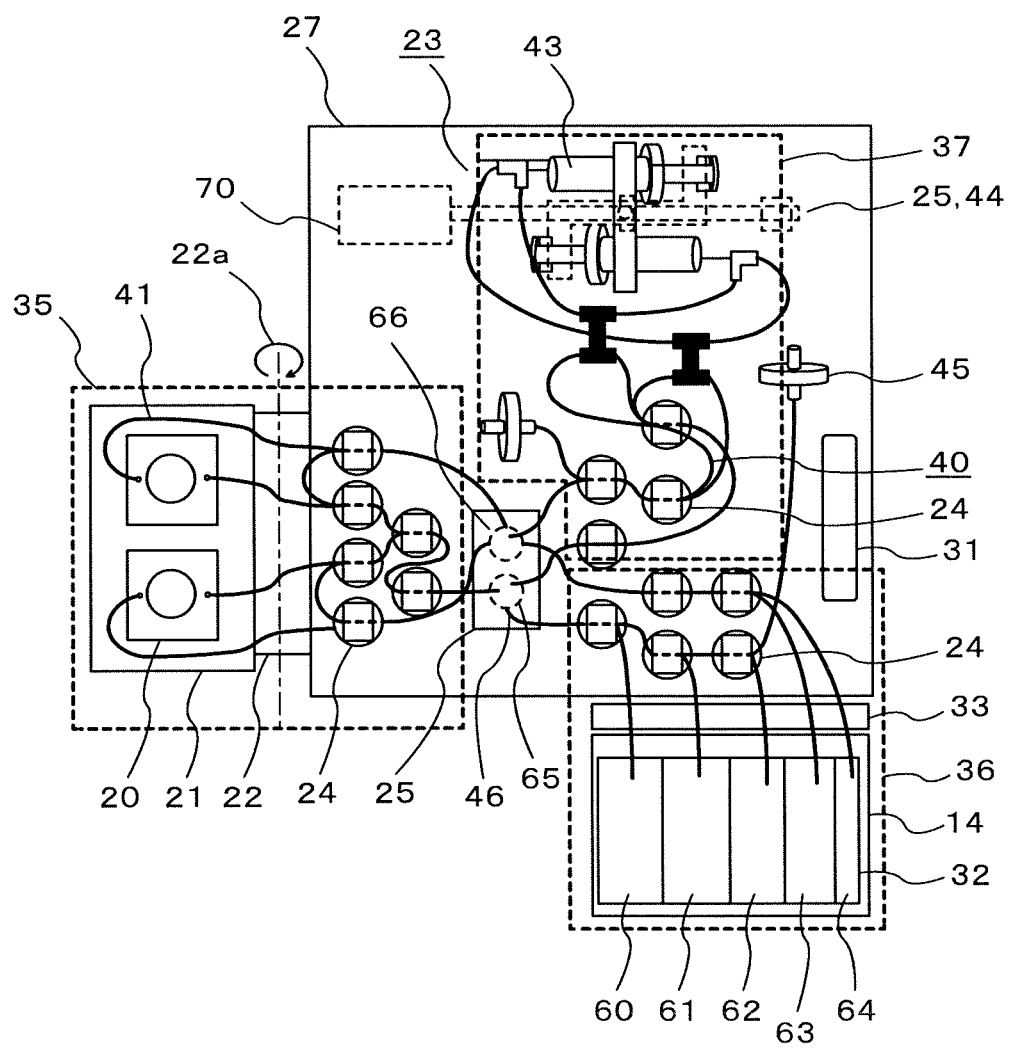
FIG. 5 is a structural top view illustrating a state in which a flow channel is mounted to a drive base according to the first embodiment.
Figure 6:
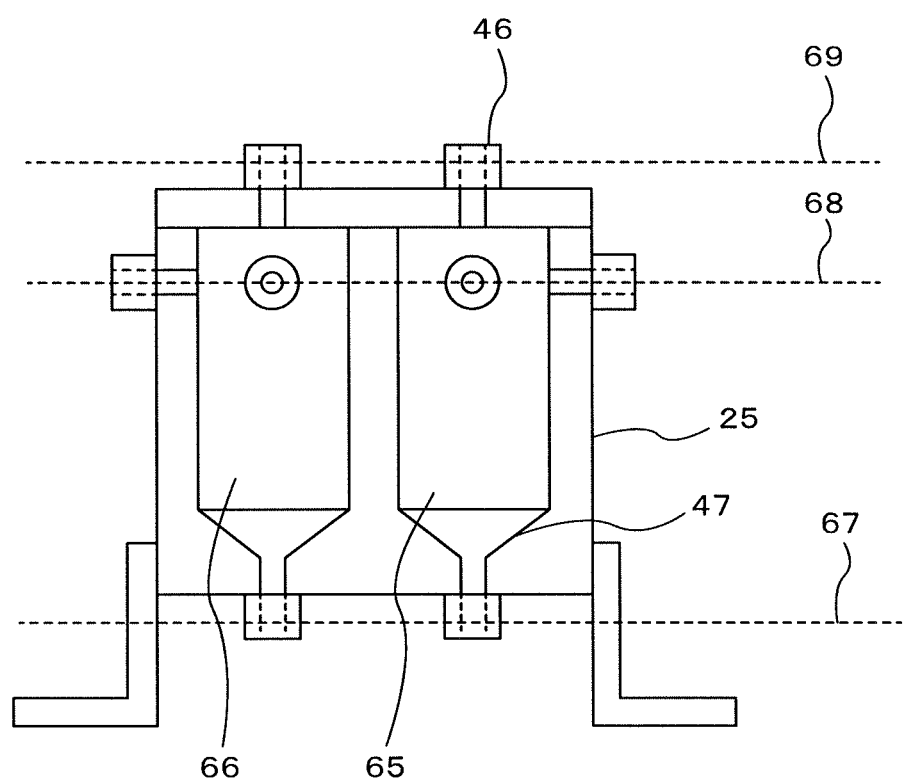
FIG. 6 is a side view illustrating a configuration of a tank according to the first embodiment.
Figure 7A:
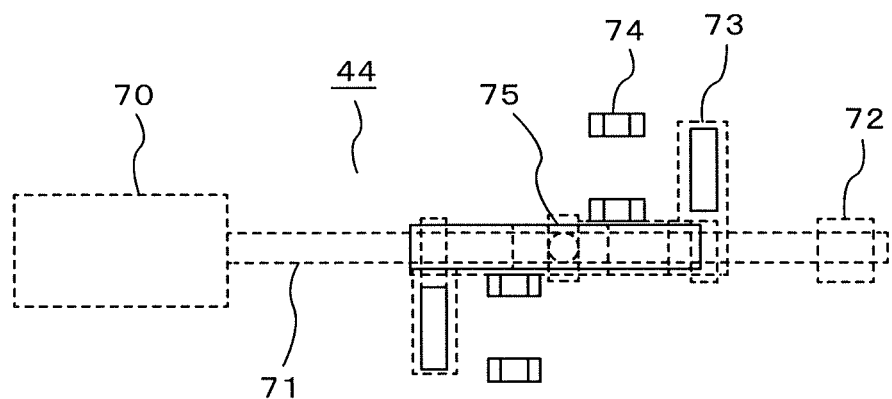
FIG. 7A is a top view illustrating a state before a pump is connected to a syringe according to the first embodiment.
Figure 7B:
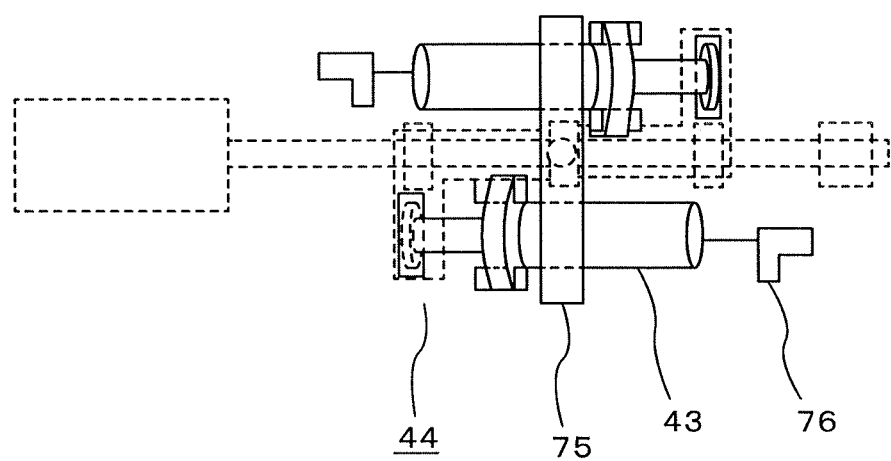
FIG. 7B is a top view illustrating a state after the pump is connected to the syringe according to the first embodiment.
Figure 7C:
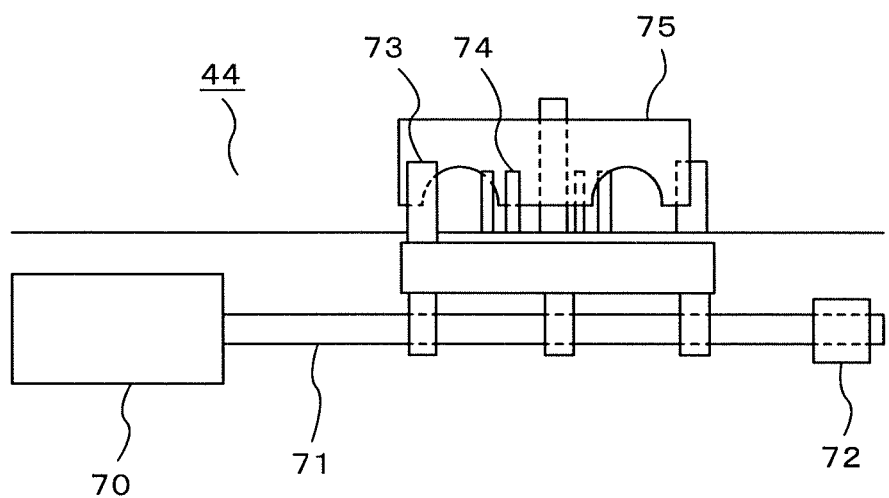
FIG. 7C is a side view illustrating a state before the pump is connected to the syringe according to the first embodiment.
Figure 7D:
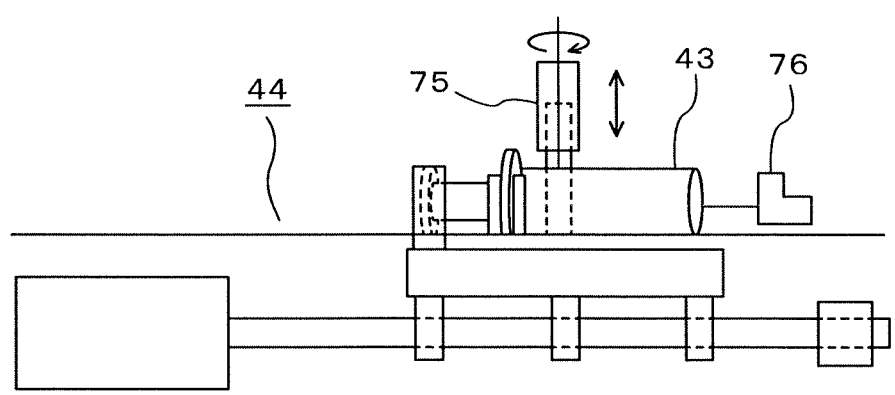
FIG. 7D is a top view illustrating a state in which the pump is currently connected to the syringe according to the first embodiment.
Figure 7E:
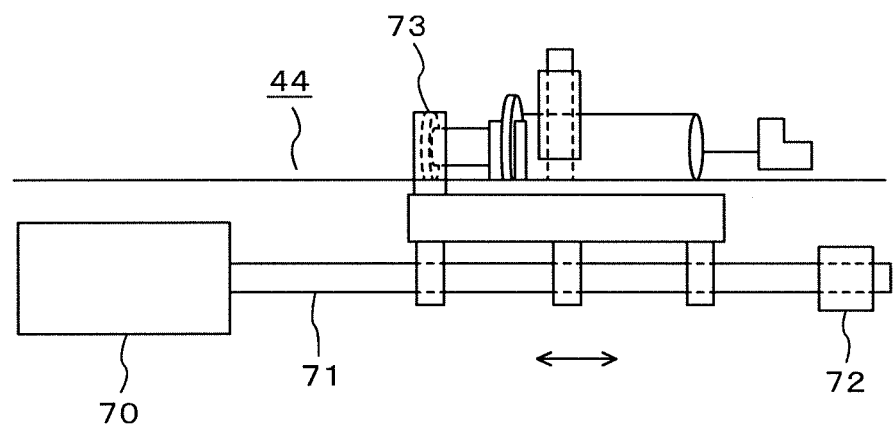
FIG. 7E is a top view illustrating a state after the pump is connected to the syringe according to the first embodiment.
Figure 8A:
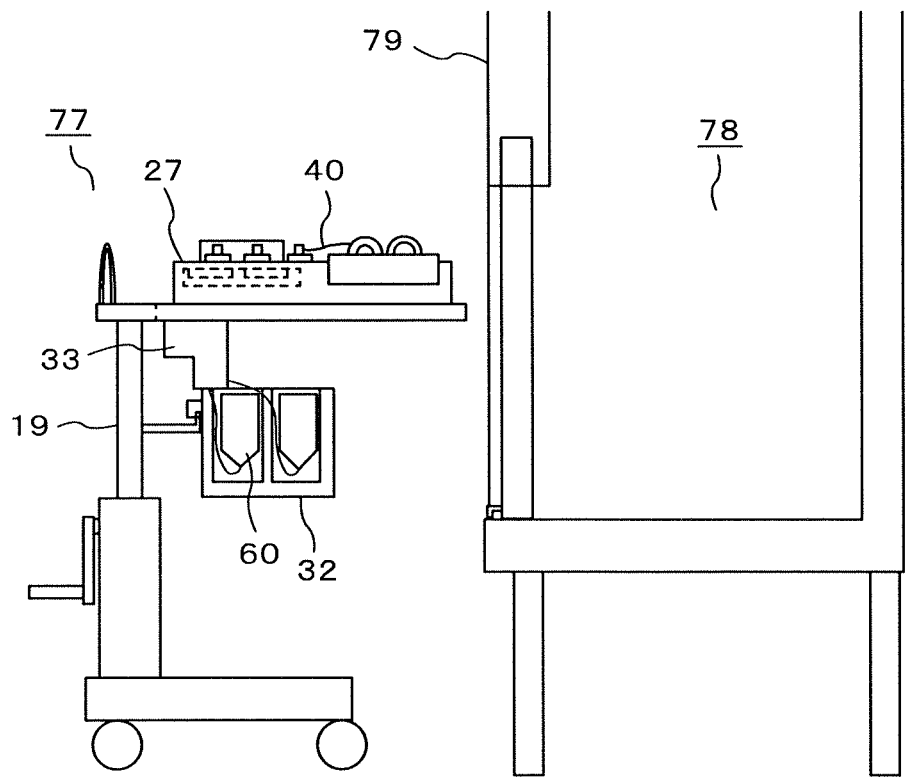
FIG. 8A is a structural side view illustrating a state in which cell suspension is not injected into a cell bag placed on a carrier jig according to the first embodiment.
Figure 8B:
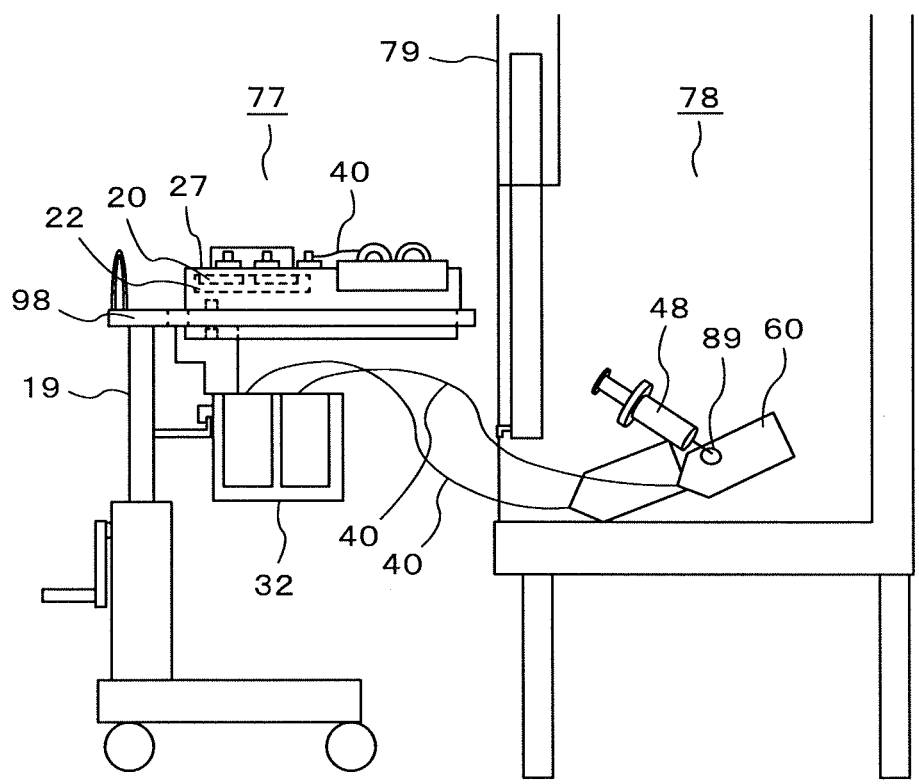
FIG. 8B is a structural side view illustrating a state in which the cell suspension is injected into the cell bag placed on the carrier jig according to the first embodiment.
Figure 9:
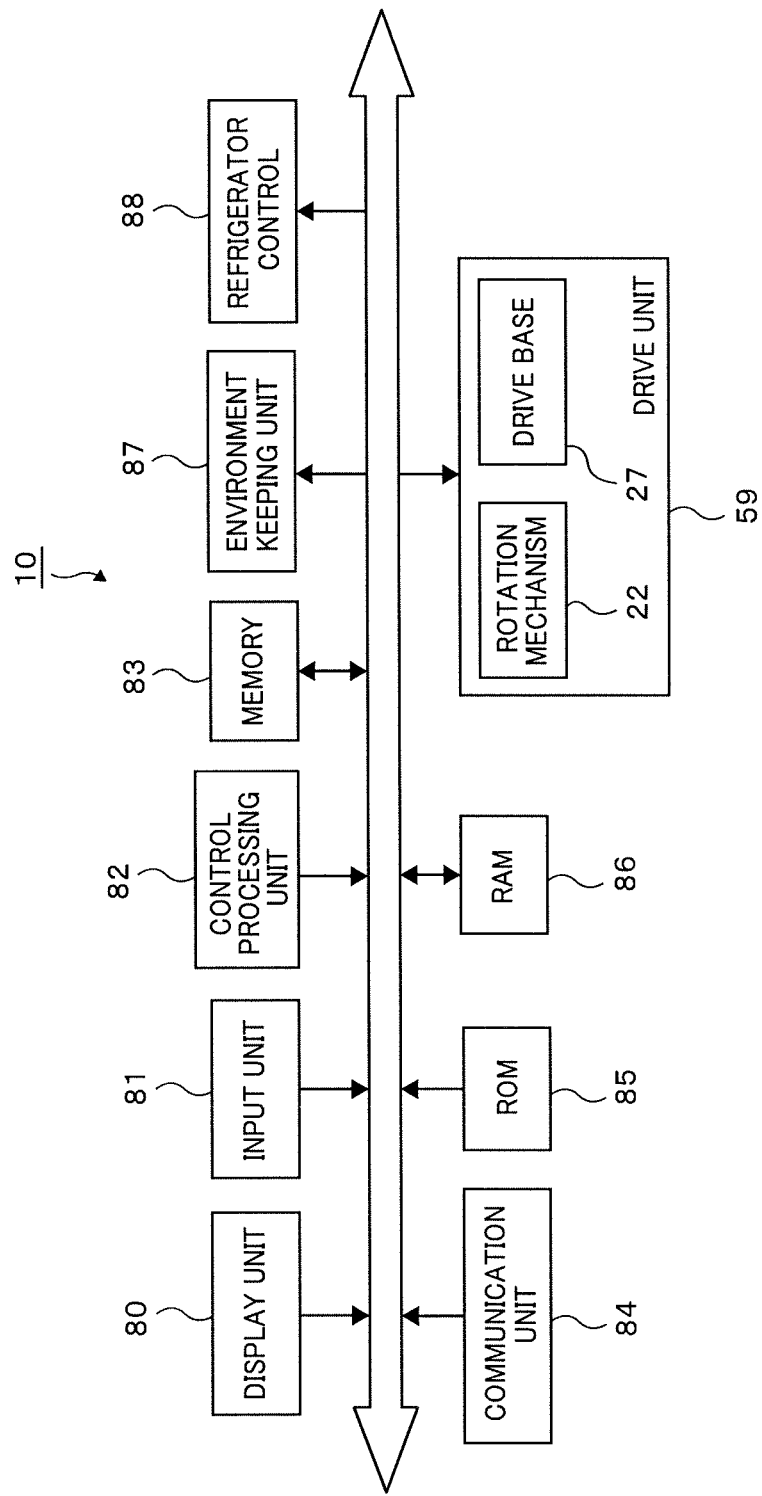
FIG. 9 is a block diagram illustrating a configuration of a control of the entire automated culture device according to the first embodiment.

FIG. 1 is a schematic view illustrating an entire configuration of an automated culture device 10 according to an example 1. FIG. 2 is a front view of the automated culture device 10. FIG. 3 is a side view of the automated culture device 10. FIGS. 4A and 4B are schematic views involved with a seal 33 between a cell culture chamber 13 and a refrigerator 14. FIG. 5 is a schematic view involved with a configuration of a flow channel 40. FIG. 6 is a schematic view involved with a tank 25 that is one of components of the flow channel 40. FIGS. 7A, 7B, 7C, 7D, and 7E are schematic views involved with a pump 23 that is one of components of the flow channel 40. FIGS. 8A and 8B are schematic views involved with an aseptic supply of culture liquid or culture medium into the flow channel 40. FIG. 9 is a block diagram illustrating a circuit for operating the automated culture device 10.

As described below one by one, the automated culture device according to the present example includes a culture medium module containing cell liquid, a culture medium, cleaning liquid, or waste liquid, which are required to be refrigerated, a pump module for feeding the liquids into the culture chamber by a pump, and warming the liquids in the tank, and a culture vessel module for supplying the cell liquid or the culture medium into a culture space in the culture vessel from the tank to execute a culture process. Each module is connected to the tank, and the respective modules are basically not connected to one another. With this structure, the flow channel can be produced for each module, and each module can be mounted to each holding base. Since each module is independent, the flow channel is organized, whereby the erroneous connection can be prevented, and space saving can be realized.

<Configuration of Automated Culture Device>

The entire configuration of the automated culture device 10 will be described with reference to FIGS. 1, 2, 3, 4A and 4B. The automated culture device 10 includes, as basic components, a cell culture chamber 13, a refrigerator 14, a control unit 15, and an intermediate chamber 16. The basic configuration of each component will be described below.

As illustrated in FIG. 1, the automated culture device 10 is composed of four sections, which are the cell culture chamber 13, the refrigerator 14 forming a refrigerating unit, the control unit 15, and the intermediate chamber 16. The inside of the automated culture device 10 can be accessed by opening a cell culture chamber door 11, a refrigerator door 12, and an intermediate chamber door 17. The cell culture chamber 13 includes a culture vessel base 21 that is a holding base or a holding tool for holding and placing the culture vessel 20, a rotating mechanism 22 that rotates as being connected to the culture vessel base, a microscope 28 for capturing a cell image in the culture vessel 20 and its stage 29, and a drive base 27 that has a drive mechanism such as a pump 23 or a valve 24, is connected to a flow channel 40 having a closed structure and including a tank 25, and serves as a holding base. The rotating mechanism 22 is fixed to one end of the drive base 27, and the culture vessel base 21 and the drive base 27 are connected via the rotating mechanism 22. A connector board 30 that connects all drive mechanisms inside and the control unit 15 is also provided. The wiring between the control unit 15 and the connector board 30 is not illustrated in the figure. During the cell culture, the cell culture chamber 13 keeps an environment close to the environment having a temperature of 37° C., a humidity of 100%, and carbon dioxide of 5%. It is to be noted that only the peripheral portion including the culture vessel 20 can keep the above-mentioned environment, according to need. The culture medium base 32 can be put into the refrigerator 14. The temperature of the cell culture chamber 13 and the refrigerator 14 can be kept by the seal 33 that passes only a tube 41 of the flow channel 40 with three sections that are the cell culture chamber 13, the refrigerator 14, and the intermediate chamber 16 being independent, whereby dew condensation can be prevented. The intermediate chamber 16 is provided with a fan 50 with a filter 51. The filter 51 is mounted to an exhaust port. The fan 50 promotes a movement of airflow to prevent humidity rise. A seal mechanism that shields the inside of the cell culture chamber 13 and the inside of the refrigerator 14 and passes only the culture liquid is provided on an inlet of the intermediate chamber 16 described later in detail. The culture medium base 32 is connected to the drive base 27 by the tube 41 passing through the seal 33.

The control unit 15 is independent of the other sections, and is provided below the cell culture chamber 13 and the intermediate chamber 16. This structure shields the temperature, humidity, and carbon dioxide in the cell culture chamber 13, and protects the inside electric devices. The control unit 15 is provided with a fan 52 that can aseptically release the inside heat to the outside by an intake filter 53 and an exhaust filter 54. The fan 52, and the filters 53 and 54 form a cooling unit of the control unit 15. Numeral 57 is a control panel for the control unit 15, and the control panel includes various buttons and a display unit, as in a general operation panel, and is used for operating the control unit 15. The control unit 15 obviously includes a central processing unit (CPU) that is a processing unit not illustrated, and a memory that is a storage unit storing a control program and data.

FIG. 2 illustrates an arrangement of each component, as viewed from front of the automated culture device 10 in which the cell culture chamber door 11 and the refrigerator door 12 are opened. The rotatable culture vessel 20 is provided in the horizontal direction, and the refrigerator 14 in which the culture medium base 32 containing cell liquid or culture medium can be mounted is provided in the vertical direction, about the drive base 27 in the cell culture chamber 13. As is apparent from FIGS. 2 and 1, in the automated culture device 10, when the space (first space) in which the drive base 27 is provided is defined as the first quadrant, the intermediate chamber 16 separating the first space and the refrigerator 14 serving as the refrigerator unit is located in the fourth quadrant, and the culture vessel base 21 that is a holding member on which the culture vessel 20 is held and placed is located in the second quadrant, or in the third quadrant by the rotation. The arrangement in the present example realizes a space-saving configuration with short distance between each component. Therefore, the culture medium stored on around 4° C. by the refrigerator 14 located in the fourth quadrant is warmed by the tank 25 on the drive base 27 located in the first quadrant, and can quickly be supplied to the culture space located in the second quadrant, whereby the cell damage caused by the movement can be minimized.

As illustrated in FIG. 2, the microscope 28 that captures a cell is provided in the vertical direction from the culture vessel 20 located in the second quadrant as viewed from front. The microscope 28 is fixed on the stage 29 for the movement and focusing. These components can all be arranged in the horizontal direction or in the vertical direction about the drive base 27 located in the first quadrant, and the optimum arrangement can be selected according to the cell to be cultured. The refrigerator 14 is arranged in the intermediate chamber 16 located in the fourth quadrant. The respective sections are separated by the seal 33, so that the cell culture chamber 13 and the space are separated except for the inside of the flow channel 40. This configuration will be described later in detail with reference to FIG. 3.

The drive base 27 is provided with the drive mechanism including the pump 23 for feeding the liquid in the flow channel 40, a valve 24 for switching the circuit for feeding the liquid, and the tank 25 that stores and warms the culture medium or the like and changes the direction of the liquid. This will be described in detail later. The connector board 30 is provided on the back surface of the drive base 27 for operating the drive mechanism, whereby the connector board can be connected to a connector 31 of the drive base 27. The connector board 30 can be wired to the control unit 15. In this case, the connector board 30 connects the connector 31 to the external control unit 15 with the environment in the cell culture chamber 13 being kept, whereby heat-insulated and waterproof structure can be realized. In this figure, the control unit 15 is provided in the vertical direction of the cell culture chamber 13. However, the control unit 15 may be arranged in the horizontal direction or in an extra space, when the device is used on a table.

FIG. 3 illustrates the arrangement of the components viewed from the side face of the automated culture device 10. In order to arrange the cell culture chamber 13 and the refrigerator 14, which have totally different environment such as temperature and humidity, are arranged in the same device, and connected to the flow channel 40, the intermediate chamber 16 and the seal 33 are provided. The cell culture chamber 13 generally has 37° C. and 100% humidity, while the refrigerator 14 generally has 4 to 5° C. inside. Therefore, when the cell culture chamber 13 is provided close to the refrigerator 14, dew condensation occurs, and temperature irregularity occurs in the cell culture chamber 13. A general incubator (cell culture chamber) and a refrigerator are designed to be supposed to be used at room temperature and indoor humidity. Since the intermediate chamber 16 for keeping the indoor condition is provided between the refrigerator 14 and the cell culture chamber 13, the occurrence of dew condensation caused by a sharp temperature change is prevented. However, it is intended that the culture medium, the cleaning liquid, and the cell suspension in the refrigerator 14 can be supplied into the cell culture chamber 13 through the tube 41 forming the flow channel 40.

In view of this, as illustrated in FIGS. 4A and 4B, the tube 41 is inserted into a groove 42 of the seal 33, and fitted to a claw 34. With this structure, the spaces of the refrigerator 14, the intermediate chamber 16, and the cell culture chamber 13 are separated, whereby the culture medium, the cleaning liquid, and the cell suspension can be supplied to the cell culture chamber 13 from the refrigerator 14. The claw 34 is respectively provided to a wall 13A that separates the cell culture chamber 13 and the intermediate chamber 16 and to a wall 14A that separates the refrigerator 14 and the intermediate chamber 16.

In FIG. 3, a cooler 18 for cooling the inside of the refrigerator 14 is provided to the refrigerator 14. The cooler 18 exhausts the cooled heat to the outside of the refrigerator 14. In order to prevent the temperature rise in the intermediate chamber 16, the air sucked by the fan 50 from the outside of the automated culture device 10 via the filter 51 is blown to the cooler 18, and then, exhausted to the outside of the automated culture device 10 via the filter 51. Specifically, the cooler 18, the fan 50, and the filter 51 form the cooling unit for the intermediate chamber 16.

An arrow 55 in FIG. 3 indicates the air flow. According to this air flow, the temperature and humidity in the intermediate chamber 16 can be kept to be equal to the outside of the automated culture device 10. Many components, such as a computer and a power supply, which generate heat, are provided in the control unit 15, so that the internal heat has to be released. The air outside the control unit 15 is introduced by the fan 52 via an intake filter 53 for keeping out dust into the control unit 15, and the air is again returned to the outside of the control unit 15 via an exhaust filter 54. FIG. 3 illustrates an air flow 56 by an arrow. This configuration can prevent dusts from scattering in a clean region such as a clean room to keep cleanness.

<Configuration of Flow Channel and Drive Base>

The configuration of the flow channel 40 and its driving method for the cell culture device according to the present example will be described with reference to FIGS. 5, 6, and 7A to 7E. FIG. 5 is a schematic view illustrating the entire configuration of the flow channel 40, the tank 25, and the drive base 27. FIG. 6 is a front view illustrating the configuration of the tank 25. FIG. 7A is a top view illustrating the state in which the syringe 43 and the pump 23 are separated, FIG. 7B is a top view illustrating the state in which the syringe 43 is set to the pump, FIG. 7C is a side view illustrating the state in which the syringe 43 and the pump 23 are separated, FIG. 7D is a side view illustrating the state in which the syringe 43 is currently set to the pump 23, and FIG. 7E is a side view illustrating the state in which the syringe 43 is set to the pump 23 to form a syringe pump 44. The syringe 43 can coaxially move. In the present example, the syringe pump is used as a drive pump. However, another pump such as a tube pump can also be used as the drive pump.

The configuration of the flow channel 40 having the closed structure will firstly be described with reference to the schematic view in FIG. 5. The flow channel 40 includes, about the tank 25, the tube 41, the culture vessel 20, the syringe 43, the filter 45, a fitting 46 to the tank 25, and a cell bag 60, a culture medium bag 61, a cleaning liquid bag 62, a waste liquid bag 63, and a collection bag 64, these bags functioning as bags for injecting liquid. These components are exchangeable. The flow channel 40 is connected to the valve 24 that serves as a drive mechanism for changing the direction of the flow, the pump 23 that feeds liquid, and the rotating mechanism 22 that rotates about the rotation shaft 22a from the horizontal direction located in the second quadrant to the vertical direction located in the third quadrant for eliminating air bubbles in the culture vessel 20, whereby cell seeding and the medium replacement by the supply of the cell liquid or the culture medium into the culture vessel 20 and the cleaning of the flow channel by the cleaning liquid can be performed. The rotation of the culture vessel base 21, serving as the holding base on which the culture vessel 20 is placed, about the rotation axis 22a from the second quadrant to the third quadrant can be realized by rotating the culture vessel base 21 downward in the counterclockwise direction from the horizontal position illustrated in FIG. 2 by the rotating mechanism 22.

The drive mechanism is arranged on the drive base 27. Since the wiring and mechanism that cannot be exposed to moisture are all put in the drive base 27, the drive mechanism can be set in a high-humidity environment. The drive base 27 is provided with the waterproof connector 31 for the connection to the control unit 15. The drive mechanism can be operated by connecting the drive base 27 to the connector 31 after the drive base 27 is mounted in the automated culture device 10.

The arrangement of the flow channel 40 is divided into three independent modules, which are the culture vessel module 35 that is the second module for feeding liquid to the culture vessel 20, the culture medium module 36 that is the first module for feeding the culture medium or the like in the refrigerator 14 to the tank 25, and a pump module 37 that is the third module for controlling the flow (direction, flow rate) of the air in order to feed liquid in the flow channel 40, about the tank 25. The formation of these modules can realize the optimum drive mechanism and the easy mounting of the flow channel. In the present example, the flow channel 40 formed by using the tube 41 connected to each of the first, the second, and the third modules from the tank 25 are sometimes referred to as first, second, and third flow channel groups. On the tube 41 forming the first, the second, and the third flow channel groups, first, second, and third valve groups including the valve 24 are formed on the drive base 27.

The configuration of the tank 25 that is the center of each of the first, the second, and the third modules according to the present example will be described with reference to FIG. 6. The tank 25 is provided with an injection tank 65 and a waste tank 66 for the culture vessel 20. The tank 25 is also provided with the fitting 46 that has different functions according to the height. The fitting 46 includes a first fitting 67, a second fitting 68, and a third fitting 69 from bottom. The first fitting 67 is used as a liquid feed port to the culture vessel 20 on the injection tank 65 and as a liquid feed port to the waste liquid bag 63 or the collection bag 64 on the waste tank 66. The second fitting 68 is used as an injection port for injecting the cell suspension or the culture medium fed from the culture medium module 36 and the cleaning liquid into the injection tank 65 on the injection tank 65, and as the injection port for injecting the waste liquid from the culture vessel 20 to the waste tank 66 on the waste tank 66. The liquid that can be injected into the tank 25 has a volume not reaching the second fitting 68. The third fitting 69 is connected to the pump module 37 and is used to control the airflow for feeding liquid into the flow channel 40. The tank 25 is formed with a taper 47 in order to prevent the cell from remaining on the wall face during the feed of the liquid. The tapered portion can prevent the cell in the cell suspension from being left in the tank 25. When the liquid is fed into the culture vessel 20 for the cell seeding and medium replacement, the liquid can temporarily be warmed to an ambient temperature in the tank 25. A heater can be provided in the injection tank 65.

The configuration of the pump will be described with reference to FIGS. 7A to 7E, taking the syringe pump 44 as an example. The syringe pump 44 is configured to include a motor 70, a ball screw 71, an encoder 72, a drive table 73, a syringe stopper 74, and a fastener 75 as illustrated in FIGS. 7A and 7C. Two syringes 43, each being provided with a valve 76 for making one-way flow of the air in the syringe 43, are mounted on the syringe stopper 74 and the drive table 73 as opposite to each other. The fastener 75 is pulled up to rotate as illustrated in FIG. 7D, whereby the syringes 43 are fixed as illustrated in FIGS. 7B and 7E. The drive table 73 moves laterally by the ball screw 71 due to the rotation of the motor 70, whereby one of the syringes can repeat the sucking operation, while the other one can repeat the exhausting operation. Thus, the continuous feed can be realized with the flow close to the laminar flow. The exhaust and the suction of the air to the tank 25 can be switched according to the arrangement of the valve 24 to the pump module 37. The syringe pump 44 can be driven with the closed structure being kept. The precise control by the encoder 72 is possible, so that the liquid can correctly be fed in a required volume.

<A Series of Operation Involved with Injection of Cell Suspension or Culture Medium to Culture Vessel>

One example of a series of a cell culture operation of the automated culture device according to the present example will be described based upon the configuration of each component described above. The cell suspension or the culture medium is fed to the injection tank 65 in the tank 25 by the syringe pump 44. When the liquid in a predetermined volume is put, air is flown from the filter 45 to eliminate the liquid in the tube 41, or the air is flown in the reverse direction to return the liquid to the original position, whereby the liquid can correctly be fed in the subsequent process. The cell suspension or the culture medium is warmed by the injection tank 25. The cell suspension or the culture medium is fed to the culture vessel 20 by the syringe pump 44 via the valve 24. In this case, the gas or waste liquid in the culture vessel 20 is sent to the waste tank 66 in the tank 25. The valve 24 in the pump module 37 is switched to send the waste liquid to the waste liquid bag 63 or the collection bag 64. The valve 24 in the pump module 37 is switched to send the cleaning liquid in the cleaning bag 62 to the injection tank 65 in the tank 25. When the cleaning liquid in the predetermined volume is injected, the air is flown from the filter 45 to eliminate the liquid in the tube 41, or the air is flown in the reverse direction to return the liquid to the original position, whereby the liquid can correctly be fed in the subsequent process. The cleaning liquid is sent to the waste tank 66 in the tank 25 via the valve 24 in order not to send the cleaning liquid to the culture vessel 20. The valve 24 in the pump module 37 is switched to send the waste liquid to the waste liquid bag 66. The operation described above is repeated a predetermined number of times during the culture period. The liquid flows in one way in the flow channel 40, particularly in the culture vessel module 35. Therefore, the waste liquid does not return to the circuit including the culture space in the culture vessel 20 and the culture medium bag 61, so that a clean and fresh culture medium is always fed to the cell. Accordingly, the cleaning environment free from bacteria can be kept.

<Liquid Injection into Flow Channel with Closed Structure>

The method of aseptically injecting the cell suspension 48 into the flow channel 40 having the closed structure according to the present example will be described with reference to FIGS. 8A and 8B. FIG. 8A illustrates the drive base 27 and the culture medium base 32 in the case where the cell suspension 48 is not injected into the flow channel 40, while FIG. 8B illustrates the state in which the cell suspension 48 is injected into the cell bag 60 in the flow channel 40.

The configuration of each component will firstly be described with reference to FIG. 8A. The drive base 27 and the culture medium base 32 on which the flow channel 40 is mounted are provided on a carrier jig 19 before they are mounted on the automated culture device 10. The carrier jig 19 can allow the drive base 27 to be mounted on or removed from the automated culture device 10. After the drive base 27 and the like is mounted to the automated culture device, only the carrier jig 19 can be removed. An empty cell bag 60 is put into the culture medium base 32. In a cell culture clean room (CPC), for example, the carrier jig 19 can be placed in a class 10,000 space 77. A directly cell processing region is only a class 100 space 78 in a safety cabinet 79 (including a clean bench) according to good manufacturing practice (GMP). Therefore, only the cell bag 60 that is thoroughly sterilized with ethanol is put into the safety cabinet 79.

As illustrated in FIG. 8B, the cell suspension 48 processed in the safety cabinet 79 is injected into the cell bag 60 from an injection port 89 by use of a syringe. After the injection, the injection port 89 is sealed to keep the closed structure of the flow channel 40. The cell bag 60 having the cell suspension 48 put therein is taken out of the class 100 space 78, and put into the culture medium base 32. The flow channel 40 preliminarily keeps the class 100 space 78 by the sterilizing process. Therefore, even if the flow channel 40 is present in class 10,000 space 77 as illustrated in FIG. 8A, the inside thereof can keep the class 100 space 78. Even if the flow channel 40 is mounted in the automated culture device 10, the inside of the flow channel 40 with the closed structure can always keep the class 100 space 78 regardless of the mounting space in the automated culture device 10, since the drive mechanism is not connected to the inside of the flow channel 40.

<Circuit Structure of Automated Culture Device>

FIG. 9 is a block diagram illustrating the structure of the control circuit for controlling the internal components of the automated culture device 10 according to the present example.

The control circuit of the automated culture device 10 includes an input unit (keyboard, mouse, etc.) 81 for inputting data or instruction, a control unit 82 for controlling each operation of the automated culture device 10, a display unit 80 that displays a control status to a user, a ROM 85 that stores a program or a parameter, a RAM 86 that temporarily stores data or processing result, a memory 83 for performing a cache operation, a communication unit 84, an environment keeping device 87 that performs the sterilizing process, the heater process, the fan process, the supply of hydrogen dioxide, and supply of water, and that includes a sensor for monitoring the condition of these processes, a driving unit 59 provided with the rotating mechanism 22 connected to the drive base 27, and a refrigerator control 88 for controlling the environment in the refrigerator.

When the user instructs the culture process to be executed from the input unit 81 or the communication unit 84, the control unit 82 sterilizes the inside of the automated culture device 10 by the sterilizing function of the environment keeping device 87 according to a culture preparation program stored in the ROM 85. After the process, a culture environment keeping process is executed to set a clean environment with temperature of 37° C., carbon dioxide concentration of 5%, and humidity of 100%, and at the same time, the refrigerator control 88 is executed. The control unit 82 then senses that the drive base 27 is set by a position sensor according to an automated culture program stored in the ROM 85. After sensing the mounting of the connector 31, the control unit 82 executes the cell culture process in the culture vessel 20 by the rotating mechanism 22 and the drive base 27. The processing condition can be displayed to the user by the display unit 80 and the communication unit 84 as needed. After the cell culture process is finished, the end of the process is reported to the user by the display unit 80 and the communication unit 84. After sensing the detachment of the drive base 27, the control unit 82 executes an ending process in accordance with an ending program stored in the ROM 85. Thus, a series of the cell culture process by the automated culture device 10 can be realized.

Example 2

A carrier device for aseptically supplying cell liquid into a flow channel with a closed structure in a cell culture device, and an aseptic method of injecting liquid such as cell liquid will be described as an example 2. In this example, the difference from the example 1 will mainly be described, and the portion same as the example 1 will not repeatedly be described.

<Liquid Injection into Flow Channel with Closed Structure>

A specific example of a carrier device and a method of injecting liquid into the flow channel with closed structure in the example 2 will be described with reference to FIGS. 8A to 8F. Specifically, an aseptic method of injecting the cell suspension 48 into the flow channel 40 having the closed structure will illustratively be described. The same injection method can be used for liquid other than the cell suspension 48.

Figure 8C:
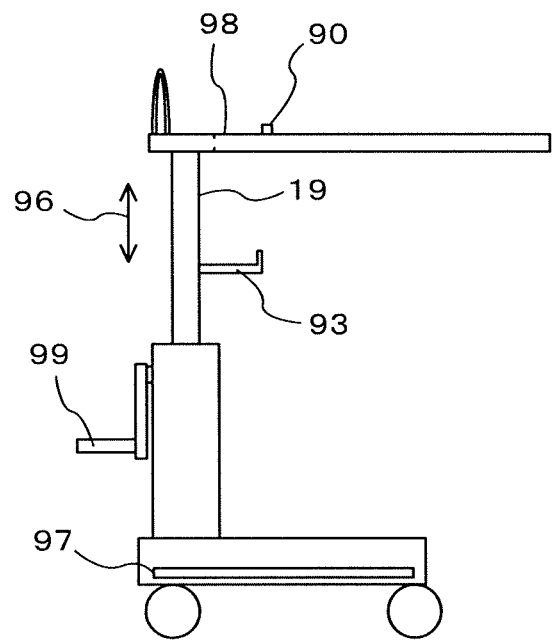
FIGS. 8CA and 8CB are structural views illustrating a configuration of a carrier device according to a second embodiment.
Figure 8C:
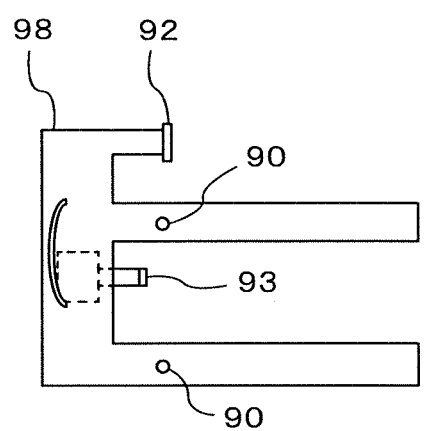
Figure 8D:
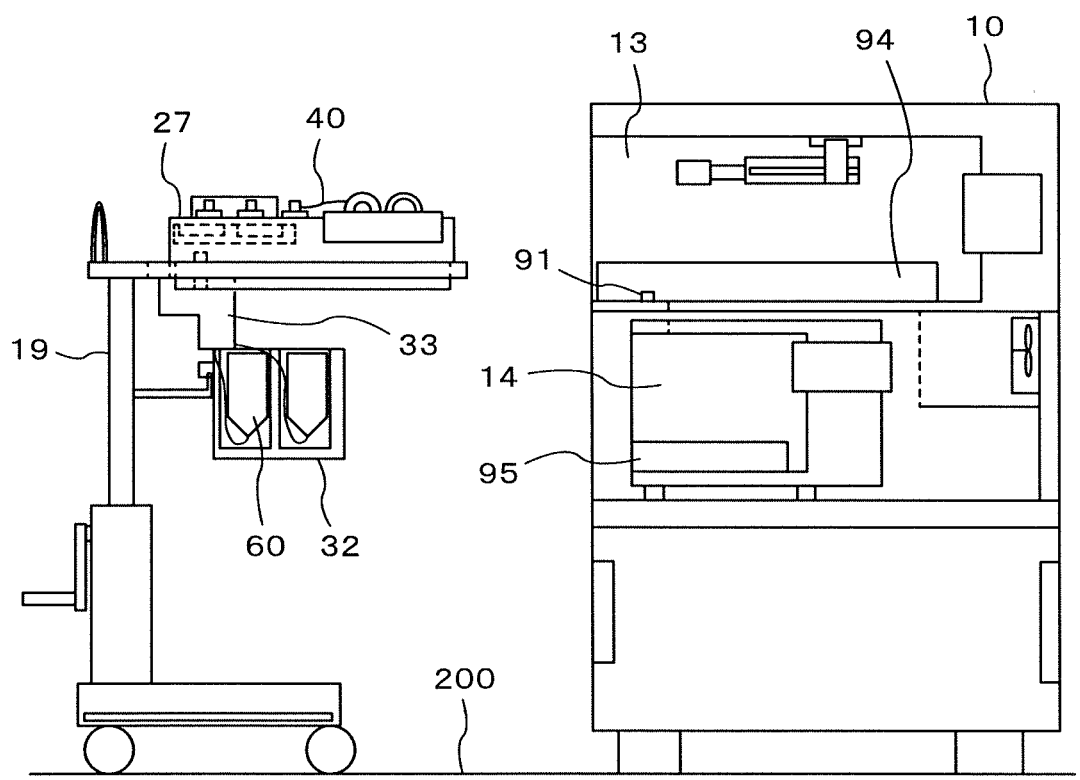
FIG. 8D is a structural side view illustrating a state before a flow channel and a drive base mounted on the carrier device are not mounted on a cell culture device according to the second embodiment.

As in the example 1, FIG. 8A illustrates the drive base 27 and the culture medium base 32 in the case where the cell suspension 48 is not injected into the flow channel 40, while FIG. 8B illustrates the state in which the cell suspension 48 is injected into the cell bag 60 in the flow channel 40. FIGS. 8CA and 8CB illustrate the configuration of the carrier jig 19 that serves as the carrier device according to the present example and that has multiple holding tools. The method of mounting the flow channel 40 and the other components to the automated culture device 10 by using the carrier jig 19 will be described with reference to FIGS. 8D, 8E, and 8F. FIG. 8D illustrates the state before the flow channel 40 and the other components are mounted to the automated culture device 10, FIG. 8E illustrates the state in which the flow channel 40 and the other components are currently mounted on the automated culture device 10, and FIG. 8F illustrates the state after the holding base including the flow channel 40 is mounted to the automated culture device 10.

FIGS. 8CA and 8CB illustrate in detail the configuration of the carrier jig 19 having the multiple holding tools according to the present example. FIG. 8CA is a side view, while FIG. 8CB is a top view. A lift 98 serving as a third holding tool for holding the drive base includes a carrier-jig-side pin 90 serving as a fixed portion, a second holding tool 92 for holding the culture vessel base, and a first holding tool 93 for holding the culture medium base. The drive base 27, the culture vessel base 21, and the culture medium base 32 can be mounted respectively on each holding tool. The lift 98 can move in a vertical moving direction 96 by a handle 99 serving as a vertical drive mechanism. The carrier jig 19 is provided with a counterweight 97 serving as a balance keeping portion, whereby the stability can be secured when the carrier jig 19 stops or moves with heavy goods being placed on the lift 98. Instead of the handle 99, an electric vertical drive mechanism such as a motor can be employed.

The method of mounting the flow channel 40 to the automated culture device 10 by use of the carrier jig 19 will be described next with reference to FIGS. 8D to 8F. As illustrated in FIG. 8D, after the process described in FIG. 8B, the carrier jig 19 located on a floor surface 200 that is an installment surface of the cell culture device 10 has mounted thereon the culture vessel base 21, the drive base 27, the culture medium base 32, and the flow channel 40, and it can be adjusted to have a height capable of being inserted into the automated culture device 10 by use of the height adjusting mechanism such as the handle 99. On the other hand, the automated culture device 10 has a drive base guide 94 and a device-side pin 91 that serve as a guide portion for a positional adjustment when the drive base 27 is inserted into the cell culture chamber 13. The automated culture device 10 also has a drive base guide 95 that serves as a guide portion for the positional adjustment when the culture medium base 32 is inserted into the refrigerator 14.

Figure 8E:
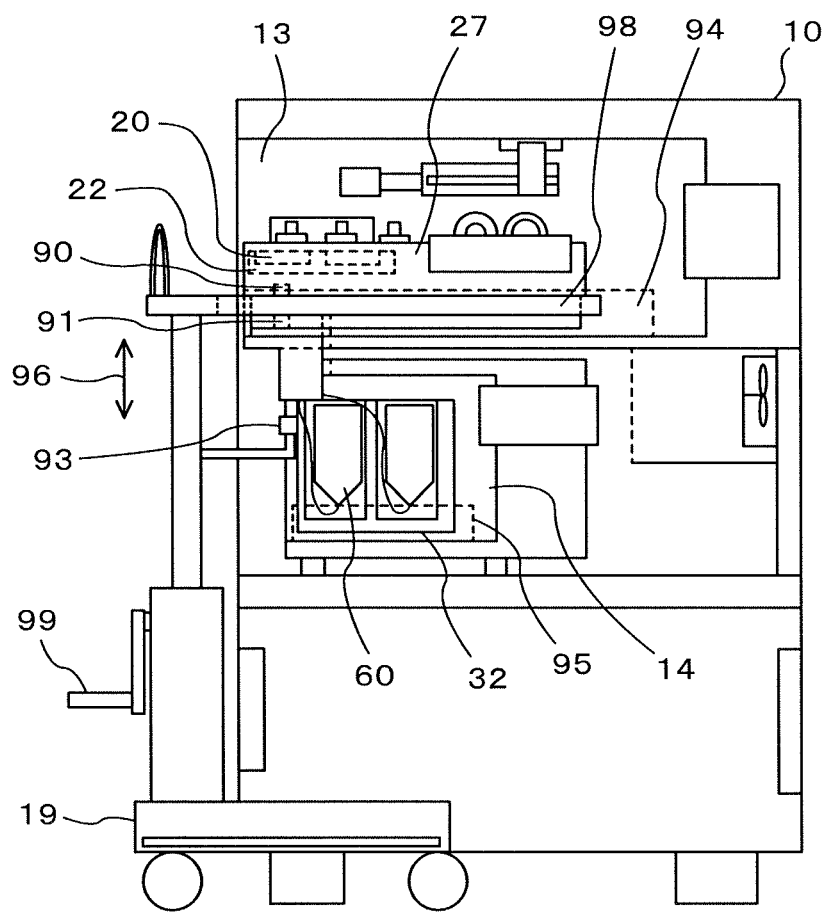
FIG. 8E is a structural side view illustrating a state in which the flow channel and the drive base are currently mounted on the cell culture device from the carrier device according to the second embodiment.
Figure 8F:
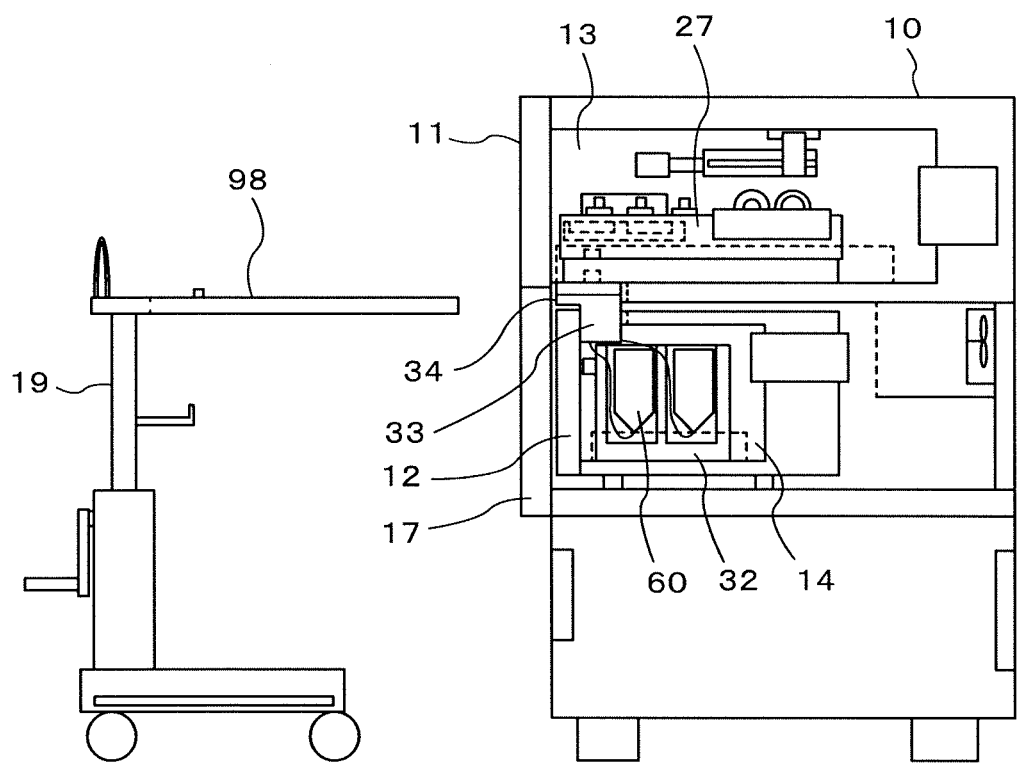
FIG. 8F is a structural side view illustrating a state after the flow channel and the drive base are mounted on the cell culture device according to the second embodiment.

When the carrier jig 19 is inserted into the automated culture device 10, the positional adjustment is made by the drive base guide 94 and the culture medium base 95, serving as the guide portion, as illustrated in FIG. 8E. In this case, the positional adjustment for mounting the culture vessel base 21 to the rotating mechanism 22 is simultaneously done. The lift 98 that is the third holding tool for holding the drive base 27 moves in the moving direction 96 by use of the handle 99, until the second holding tool 92 holding the culture vessel base and the culture vessel base claw 100 illustrated in FIG. 1 are separated, the pin 90 is separated from the drive base 27 and connected to the pin 91, and the first holding tool 93 holding the culture medium base is separated from the culture medium base 32. Thereafter, the carrier jig 19 provided with the first, second, and third holding tools are removed from the automated culture device 10. Then, the culture vessel base 21 is mounted to the rotating mechanism 22, the drive base 27 is mounted in the cell culture chamber 13, and the culture medium base 32 is mounted in the refrigerator 14, simultaneously, as illustrated in FIG. 8F. In this case, the seal 33 is mounted on the claw 34 (see FIG. 4A). Then, the cell culture chamber door 11, the refrigerator door 12, and the intermediate chamber door 17 are closed to execute the automatic culture process. After the automatic culture process, the processes in FIGS. 8F, 8E, and 8D are executed in this order, whereby the culture vessel base 21, the drive base 27, and the culture medium base 32 can be removed by the carrier jig 19 as being held by the corresponding holding tools.

The examples of the present invention have been described above. The present invention is not limited to the above-mentioned examples, and various modifications are included. As described previously, various modifications are possible, for example, the tube pump can be used as the driving pump, instead of the syringe pump. The examples descried above are described in detail for better understanding of the present invention, and the present invention is not limited to the one including all components described above.

A part or all of components, functions, and processing units of the above-mentioned automated culture device may obviously be realized by hardware including an integrated circuit. Alternatively, a part or all of them may obviously be realized by software by creating a program executed by a CPU that is a processing unit.

Claims involved with various inventions described in the specification are described in claims, but the inventions described in the present specification are not limited thereto, and various inventions including the inventions described below are described.

*1

A liquid injecting method for injecting cell liquid into a cell bag that is carried to a cell culture device, the method comprising: carrying a carrier device to a vicinity of a directly cell processing region, the carrier device including a holding tool for holding a culture medium base having multiple bags including the cell bag, and a first flow channel group that supplies the culture medium and the cell from some of the multiple bags and exhausts the culture medium and the cell to the other some of the multiple bags, a culture vessel base including a culture vessel that cultures the cell, and a second flow channel group that supplies the culture medium and the cell to the culture vessel, and exhausts the culture medium and the cell from the culture vessel, and a drive base provided with a pump unit that controls the supplied volume of the culture medium and the cell in the flow channel of the first and second flow channel groups; moving the cell bag connected to the flow channel to the directly cell processing region from the culture medium base, and injecting the cell into the cell bag in the directly cell processing region; and mounting the cell bag after the injection of the cell on the culture medium base, and then, carrying the same to the cell culture device.

*2

The liquid injecting method according to *1, wherein the cell bag has an injection port into which the cell is injected, and the cell is injected through the injection port.

*3

The liquid injecting method according to *1, wherein after the carrier device is carried to the cell culture device, the culture medium base, the culture vessel base, and the drive base are removed from the holding tool, and are mounted into the cell culture device.

*4

The liquid injecting method according to *1, wherein the directly cell processing region is a class 100 space, and a place where the cell culture device is provided is a class 10000 space.

REFERENCE SIGNS LIST

10 . . . automated culture device,
11 . . . cell culture chamber door,
12 . . . refrigerator door,
13 . . . cell culture chamber,
14 . . . refrigerator,
15 . . . control unit,
16 . . . intermediate chamber,
17 . . . intermediate chamber door,
18 . . . cooler,
19 . . . carrier jig,
20 . . . culture vessel,
21 . . . culture vessel base,
22 . . . rotating mechanism,
23 . . . pump,
24 . . . valve,
25 . . . tank,
27 . . . drive base,
28 . . . microscope,
29 . . . stage,
30 . . . connector board,
31 . . . connector,
32 . . . culture medium base,
33 . . . seal,
34 . . . claw,
35 . . . culture vessel module (second module),
36 . . . culture medium module (first module),
37 . . . pump module (third module),
40 . . . flow channel,
41 . . . tube,
42 . . . groove,
43 . . . syringe,
44 . . . syringe pump,
45 . . . filter,
46 . . . fitting,
47 . . . taper,
48 . . . cell suspension,
50 . . . fan (intermediate chamber),
51 . . . filter (intermediate chamber),
52 . . . fan (control unit),
53 . . . intake filter,
54 . . . exhaust filter,
55 . . . air flow (intermediate chamber), 56 . . . air flow (control unit),
57 . . . control panel (control unit),
59 . . . drive unit,
60 . . . cell bag,
61 . . . culture medium bag,
62 . . . cleaning liquid bag,
63 . . . waste liquid bag,
64 . . . collection bag,
65 . . . injection tank,
66 . . . waste tank,
67 . . . first fitting,
68 . . . second fitting,
69 . . . third fitting,
70 . . . motor,
71 . . . ball screw,
72 . . . encoder,
73 . . . drive table,
74 . . . syringe stopper,
75 . . . fastener,
76 . . . valve,
77 . . . class 10000 space,
78 . . . class 100 space,
79 . . . safety cabinet,
80 . . . display unit,
81 . . . input unit,
82 . . . control unit,
83 . . . memory,
84 . . . communication unit,
85 . . . ROM,
86 . . . RAM,
87 . . . environment keeping device,
88 . . . refrigerator control,
89 . . . injection port,
90 . . . pin (on carrier jig),
91 . . . pin (on cell culture device),
92 . . . holding tool for culture vessel base,
93 . . . holding tool for culture medium base,
94 . . . drive base guide,
95 . . . culture medium base guide,
96 . . . moving direction (vertical),
97 . . . counterweight (weight),
98 . . . lift,
99 . . . handle,
100 . . . culture vessel base claw,
200 . . . floor surface

The invention claimed is:

1. A cell culture device for culturing a cell by using a culture medium, the device comprising:
a plurality of flow channels including a first flow channel group, a second flow channel group, and a third flow channel group;
a first module including multiple bags having the culture medium and the cell, and the first flow channel group including a first plurality of flow channels that supplies the culture medium and the cell from some of the multiple bags and a second plurality of flow channels that exhausts the culture medium and the cell to some other bags of the multiple bags;
a second module including a culture vessel for culturing the cell, and the second flow channel group including a third plurality of flow channels that supplies the culture medium and the cell to the culture vessel and a fourth plurality of flow channels that exhausts the culture medium and the cell from the culture vessel;
a tank unit including an injection tank that holds the culture medium and the cell supplied from a first flow channel in the first plurality of flow channels in the first flow channel group, the first flow channel being disposed in connecting arrangement between an output of the multiple bags having the culture medium and the cell and an input to the injection tank, and allows the held culture medium and the cell to flow out to a second flow channel in the third plurality of flow channels in the second flow channel group in order to supply the culture medium and the cell to the culture vessel, and a waste tank that holds the culture medium and the cell, which are exhausted from the culture vessel and flown from a fourth flow channel in the fourth plurality of flow channels in the second flow channel group, and allows the held culture medium and the cell to flow out to a third flow channel in the second plurality of flow channels in the first flow channel group in order to exhaust the culture medium and the cell to the some other bags of the multiple bags, wherein the third flow channel is disposed in connecting arrangement between an output of the waste tank and the some other bags of the multiple bags, and
a third module including a pump unit that controls a volume of the supplied culture medium and the cell in the flow channels in the first and second flow channel groups and a volume of the culture medium and the cell held in the tank unit;
wherein the first module, the second module, and the third module are connected to the tank unit via the first flow channel group, the second flow channel group, and the third flow channel group, respectively.

2. The cell culture device according to claim 1, comprising:
a holding base on which the first module, the second module, and the third module are placed.

3. The cell culture device according to claim 2, wherein the holding base is detachable to the cell culture device.

4. The cell culture device according to claim 2, wherein the holding base includes a culture medium base that holds the multiple bags, a culture vessel base that holds the culture vessel, and a drive base that holds the pump unit, and the drive base further includes a valve that changes a flow rate and a flow direction of the culture medium and the cell in the first and second flow channel groups.

5. The cell culture device according to claim 4, further comprising:
a control unit that controls the pump unit and the valve.

6. The cell culture device according to claim 2, wherein the holding base includes a culture medium base that holds the multiple bags, a culture vessel base that holds the culture vessel, and a drive base that holds the pump unit, and the culture medium base, the culture vessel base, and the drive base are detachable to the cell culture device.

7. The cell culture device according to claim 2, wherein the second flow channel group is connected to a feed port and an exhaust port formed on the culture vessel.

8. The cell culture device according to claim 1, wherein the first module, the second module, and the third module are detachable to the cell culture device.

9. The cell culture device according to claim 1, wherein the pump unit includes a syringe pump or a tube pump.

10. The cell culture device according to claim 1, wherein the first module, the second module, and the third module are connected to the tank unit without being connected to each other.

11. The cell culture device according to claim 1, wherein the pump in the third module is the only pump in the cell culture device.

12. The cell culture device according to claim 1, wherein the injection tank and the waste tank are independent of each other.

13. A carrier device that can carry multiple bags for a culture medium and a cell to a cell culture device, and that is detachable to the cell culture device, the carrier device comprising:
   a plurality of flow channels including a first flow channel group, a second flow channel group, and a third flow channel group;
   a first holding tool on which a culture medium base is disposed, the culture medium base including multiple bags having the culture medium and the cell, and the first flow channel group including a first plurality of flow channels disposed in connecting arrangement between outputs of the multiple bags having the culture medium and the cell and an input to an injection tank, the first plurality of flow channels supplying the culture medium and the cell from some of the multiple bags to the injection tank, and a second plurality of flow channels disposed in connecting arrangement between a waste tank and some other bags of the multiple bags, the second plurality of flow channels exhausting the culture medium and the cell to the some other bags of the multiple bags;
   a second holding tool that holds a culture vessel base including a culture vessel for culturing the cell, and the second flow channel group including a third plurality of flow channels that supplies the culture medium and the cell to the culture vessel and a fourth plurality of flow channels that exhausts the culture medium and the cell from the culture vessel, and
   a third holding tool that holds a drive base including a pump unit that controls a volume of the supplied culture medium and the cell in the flow channels in the first and second flow channel groups, and a tank unit including an injection tank that holds the culture medium and the cell supplied from a first flow channel in the first plurality of flow channels in the first flow channel group, the first flow channel being disposed in connecting arrangement between an output of the multiple bags having the culture medium and the cell and an input to the injection tank, and allows the held culture medium and the cell to flow out to a second flow channel in the third plurality of flow channels in the second flow channel group in order to supply the culture medium and the cell to the culture vessel, and a waste tank that holds the culture medium and the cell, which are exhausted from the culture vessel and flown from a fourth flow channel in the fourth plurality of flow channels in the second flow channel group, and allows the held culture medium and the cell to flow out to a third flow channel in the second plurality of flow channels in the first flow channel group in order to exhaust the culture medium and the cell to the some other bags of the multiple bags, wherein the third flow channel is disposed in connecting arrangement between an output of the waste tank and the some other bags of the multiple bags;
   wherein the first module, the second module, and the third module are connected to the tank unit via the first flow channel group, the second flow channel group, and the third flow channel group, respectively.

14. The carrier device according to claim 13, wherein the third holding tool has a fixed portion for fixing a position where the drive base is held.

15. The carrier device according to claim 13, wherein the first and third holding tools are configured to attach or detach the culture medium base and the drive base to or from the cell culture device along a guide portion formed in the cell culture device.

16. The carrier device according to claim 13, further comprising:
   a drive mechanism for changing a distance between the first, second, and third holding tools and a contact surface of the carrier device,
   wherein the drive mechanism changes the distance with the contact surface to detach the culture medium base, the culture vessel base, and the drive base from the first, second, and third holding tools respectively, and attaches these bases into the cell culture device, when the carrier device is inserted into the cell culture device.

17. The carrier device according to claim 13, comprising:
   a balance keeping unit for stabilizing a standing position of the carrier device.

18. The carrier device according to claim 13, wherein the second holding tool is connected to the third holding tool via a rotating mechanism.

19. The carrier device according to claim 13, wherein the first module, the second module, and the third module are connected to the tank unit without being connected to each other.

20. The carrier device according to claim 13, wherein the pump in the third module is the only pump in the carrier device.

21. The carrier device according to claim 13, wherein the injection tank and the waste tank are independent of each other.

* * * * *